United States Patent

Tsitlik et al.

[11] Patent Number: 5,902,229
[45] Date of Patent: May 11, 1999

[54] DRIVE SYSTEM FOR CONTROLLING CARDIAC COMPRESSION

[75] Inventors: Joshua E. Tsitlik, Cliffside Park; Howard R. Levin, Teaneck, both of N.J.; Naum Ziselson, Baltimore, Md.; Paul C. Michelman, New York, N.Y.

[73] Assignee: Cardio Technologies, Inc., Pine Brook, N.J.

[21] Appl. No.: 09/052,037

[22] Filed: Mar. 30, 1998

[51] Int. Cl.[6] .................................................. A61M 1/12
[52] U.S. Cl. .............................................................. 600/46
[58] Field of Search .................................. 600/16, 17, 18

[56] References Cited

U.S. PATENT DOCUMENTS 4,794,910  1/1989  Mushika ........................................ 600/18

Primary Examiner—William E. Kamm
Attorney, Agent, or Firm—Darby & Darby

[57] ABSTRACT

An inflation system for independently controlling the rise time and plateau level of a pressure profile applied to an inflatable chamber includes a pneumatic source disposed in fluid communication with a pressure path including a regulation device for establishing respective high and low pressure levels. A supply mechanism is disposed at the output of the pressure path and is operative to alternately expose the inflatable liner to the high and low pressure levels to define an independently controllable rise time.

31 Claims, 9 Drawing Sheets

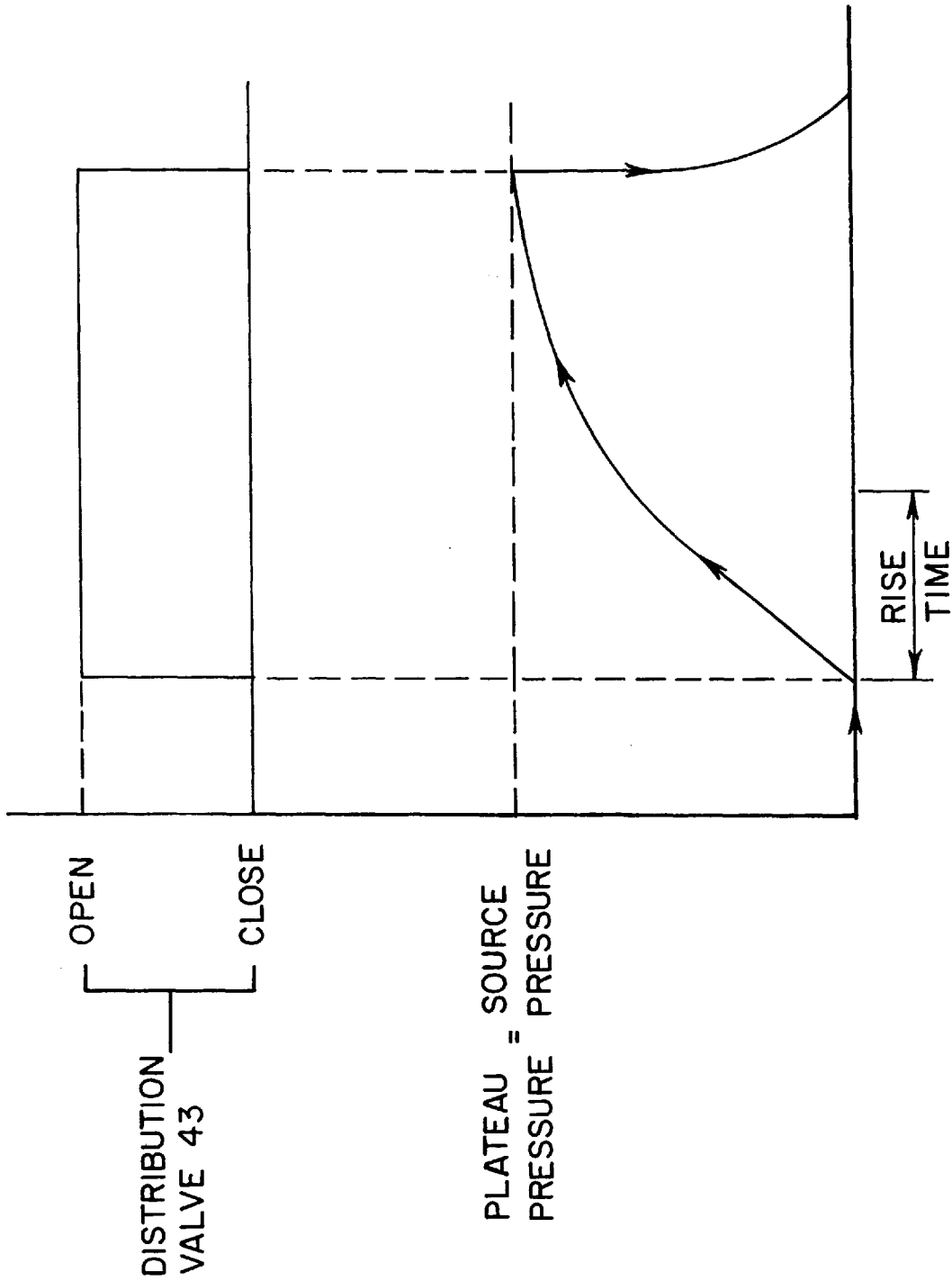

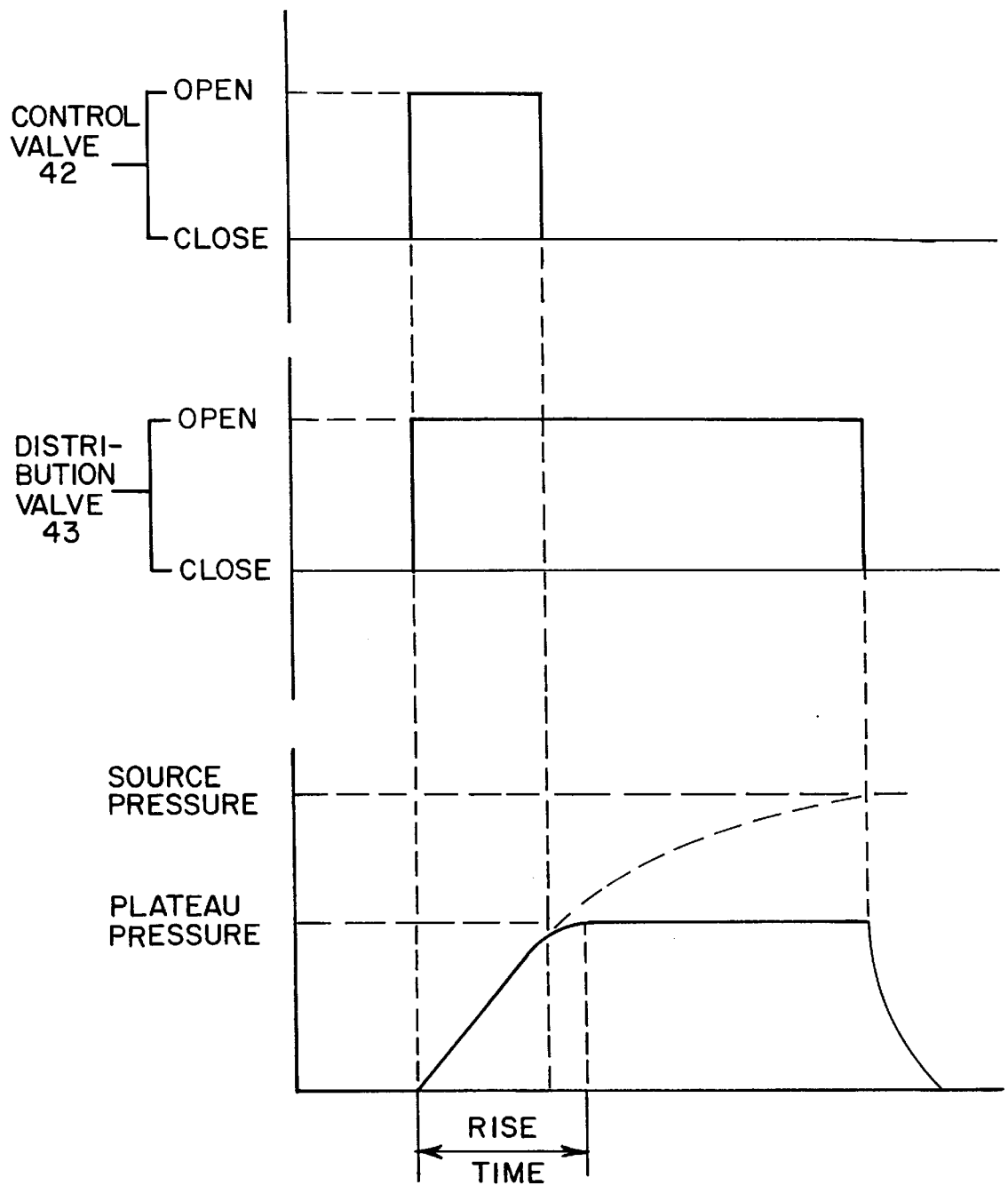

FIG. 9
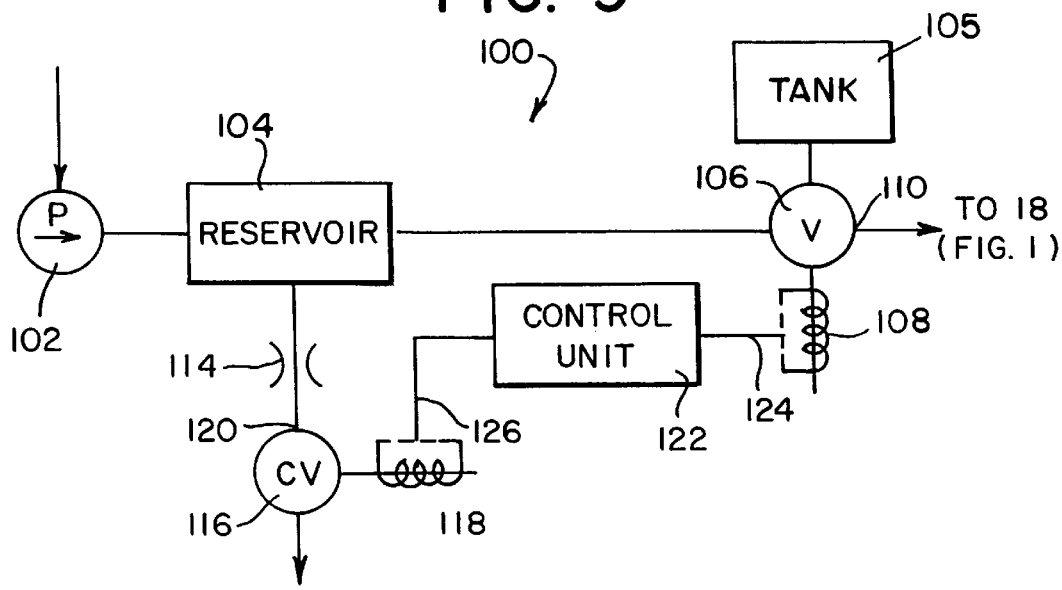
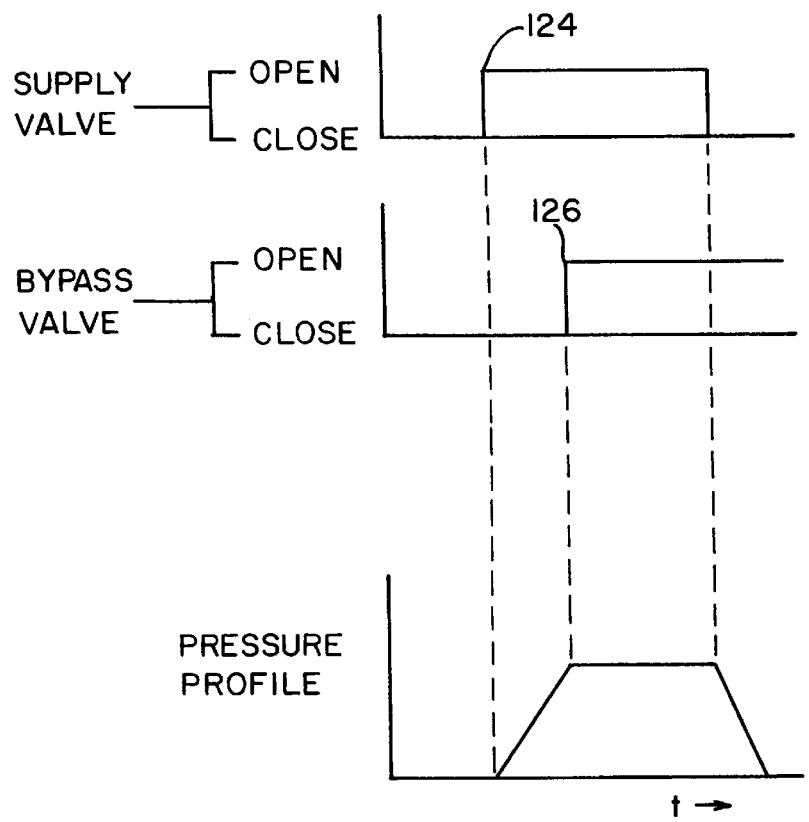
FIG. 10

DRIVE SYSTEM FOR CONTROLLING CARDIAC COMPRESSION

BACKGROUND OF THE INVENTION

1. Field of the Invention

The present invention relates to systems for mechanically assisting the heart and more particularly to a drive system capable of controlling the rise time and plateau level of a pressure pulse applied to a cardiac compression apparatus.

2. Discussion of the Related Art

Heart disease accounts for one of the leading causes of cardiac dysfunction among individuals worldwide. One of the more common heart disorders often associated with heart disease involves substantial weakening of the heart. Left unaided, a critically weakened heart often cannot pump the necessary blood required to sustain bodily functions.

An important life-saving technique for individuals diagnosed with weakened hearts includes mechanically assisting the heart to pump blood. Such support ensures an adequate blood pressure for sufficiently supplying blood throughout the body without undue stress on the heart muscle. Typically, a device such as a heart compression apparatus carries out the assistance during invasive surgery. An alternative device incorporating cardiopulmonary resuscitation (CPR) techniques externally compresses the chest to rhythmically squeeze the heart area and assist in increasing blood flow.

Those skilled in the art have proposed a variety of devices to successfully carry out the heart compression function to maximize support for the heart and provide reliable and accurate functionality. One such device, disclosed in pending Provisional U.S. patent spplication Ser. No. 60/028,722, filed on Oct. 18, 1996 and assigned to the assignee of the present invention, carries and supports the heart during invasive surgery while uniformly applying pressure directly to the heart through means of an inflatable liner. The liner is cyclically inflated and deflated by an inflation system to apply pressure to the heart.

Because each heart pumps blood according to a pressure profile unique for each patient, successful cardiac compression on the inflatable liner depends upon the inflation system being controllable to somewhat match the patient's personal cardiac rhythm or pressure profile. An important consideration is the sharp rise in ventricular pressure during the early portion of systole, which provides only about fifty to one hundred milliseconds within which to establish synchronous compression.

One conventional inflation system for controlling the rise time and plateau level of a pressure pulse utilizes a single regulator-reservoir configuration. The system includes a compressor connected to a regulator, and a reservoir disposed downstream of the regulator. An outflow valve connects to the reservoir outlet and is placed in fluid communication with an inflation chamber disposed in a cardiac compression apparatus for supporting and assisting a heart. During operation, the compressor supplies flow through the regulator, which maintains a desired pressure in the tank. Inflation of the chamber occurs by opening the outflow valve to produce an exponentially increasing pressure transient within the chamber that asymptotically approaches the supply pressure level to define a relatively constant pressure, or plateau level, within a known response time.

While this system works relatively well to ensure that the pressure applied to the liner never exceeds the supply pressure, the configuration provides a relatively accurate adjustment of the plateau level without any independent control over changes in the rise time of the start transient. Generally, the waveforms may be expressed as:

$$P = P_{PLATEAU} * [1 - \exp(-t/T)]$$

wherein t represents time, and T represents the system time constant. As illustrated in FIG. 3, regardless of the plateau setting, the time constant T remains unchanged with changes only in the magnitude of the plateau level. Because of this characteristic, control of the rise time using the conventional inflation system is generally possible only by affecting the system resistances, capacitances, or source regulator pressure. As a result, the response of the transient to reach the plateau level is typically of the order of three time constants. The rise time, known commonly as the time required to reach the plateau level, generally depends upon system characteristics such as overall resistance and capacitance. Therefore, having the capability of merely controlling the plateau level does not enable independent control over the rise time.

Moreover, because of the controlled conditions associated with surgical environments, the conventional inflation system is often disposed several feet from the inflation chamber. As a result, a relatively long hose generally couples the inflation system to the compression apparatus liner. Coupled with the effects of overall system resistances and pressure load, the resulting time constant realized by the conventional inflation system substantially degrades system performance. Alternatively, should the resistance be lowered through expansion of the tubing diameter, the size, weight and cost for the components required to effect a larger flowrate would render the system undesirable from a practical standpoint.

A second proposal solves several of the aforementioned problems by implementing a source pressure substantially higher than the desired plateau pressure. The pressure circuit is similar to the first proposal described above, but includes an additional control valve disposed in series with the outflow valve. Operation of the system depends upon precise timing to initially open both valves simultaneously, exposing the liner to an exponentially increasing pressure characteristic of the source pressure level, then closing the control valve upon reaching a desired plateau pressure and trapping the pressure within the liner for a timed duration.

While this proposal is somewhat beneficial in offering a way of controlling the rise time independently of the desired plateau pressure, the precise timing required to effectively control the plateau level by closing the control valve at precisely the right instant is difficult in practice to achieve. This is typically due to the equilibrium time required from the instant the valve closes until the plateau pressure is actually realized. As a result, the system often exhibits an undesirable overshoot or undershoot of the plateau pressure causing an unexpected deviation in the cardiac compression apparatus liner.

Therefore, those skilled in the art have recognized the need for an inflation system capable of following a predefined pressure profile with independent control of both rise time and plateau level with a minimum number of components and accurate repeatability. The inflation system of the present invention satisfies these needs.

SUMMARY OF THE INVENTION

The inflation system of the present invention provides a straightforward means of inflating a cardiac compression apparatus according to a predefined pressure profile and having an independently controllable rise time and plateau level. Additionally, the system incorporates a minimum number of components to minimize size and associated procurement and operating costs.

To realize the advantages noted above, the inflation system of the present invention, according to a first embodiment, independently controls the rise time and plateau level of a pressure cycle profile applied to an inflatable chamber. In one form, the invention includes a pneumatic source for pressurizing fluid at a predetermined pressure and a pressure path disposed in fluid communication with the source. The pressure path includes a regulation device for establishing respective high and low pressure levels. A supply mechanism disposed at the output of the pressure path is operative to alternately expose the chamber to the high and low pressure levels according to predetermined switchable durations to define the rise time and plateau levels.

In another form, the present invention comprises a heart assistance system for supporting and assisting the cyclic pumping of a heart. The heart assistance system includes a cardiac compression apparatus having a support cup and an internal inflation chamber for uniformly compressing the heart. An inflation system applies a pressure pulse to the inflation chamber and places the heart in cyclic compression by independently controlling the rise time and the plateau level of the pressure pulse. The inflation system includes a pneumatic source for pressurizing fluid at a predetermined pressure and a pressure path disposed in fluid communication with the source. The pressure path includes a regulation device for establishing respective high and low pressure levels. A supply mechanism disposed at the output of the pressure path is operative to alternately expose the chamber to the high and low pressure levels according to predetermined switchable durations to define the rise time and plateau levels.

In yet another form, the invention comprises a method of independently controlling the rise time and the plateau level of a pressure cycle applied to an inflatable chamber. The method includes the steps of exposing the chamber to a first pressure from a pressure reservoir to exponentially increase the pressure within the chamber for a controllable duration defining the rise time; and switching the pressure in the reservoir following expiration of the duration to a constant second pressure defining the plateau level.

In still yet another form, the present invention includes a source pressure substantially higher than the desired plateau pressure. The pressure circuit includes two outlet lines from the tank. One outlet line has a switching valve that switches between a first regulated high pressure line and a second regulated plateau pressure line. The second output line is connected to the compression apparatus liner through a supply valve. Operation of the system depends upon precise timing of the switching valve to, first, expose the liner to the high pressure level which is greater than the plateau pressure level, then switching the valve upon reaching a desired predetermined percentage of the plateau pressure, thereby fluidly connecting the liner to the plateau pressure. The supply valve is then switched to close (to vent the liner to atmosphere) at the end of the systolic cycle.

Other features and advantages of the present invention will be apparent from the following detailed description when read in conjunction with the accompanying drawings.

BRIEF DESCRIPTION OF THE DRAWINGS

FIGS. 3A and 3B are timing diagrams for the conventional inflation system of FIGS. 2A and 2B, respectively;

FIG. 9 is a block diagram of an inflation system according to a third embodiment of the present invention;

FIG. 10 is a timing diagram for the inflation system of FIG. 9 illustrated with respect to a portion of a pressure profile;

DETAILED DESCRIPTION OF THE INVENTION

The inflation system of the present invention independently controls the rise time and plateau level of a pressure profile by switching between first and second pressure levels with a minimum number of components. The control of the rise time and plateau level is important to provide a satisfactory response time to properly match the pressure pulses of a mechanical heart assistance system with the natural pulses of the pumping heart.

Figure 1:
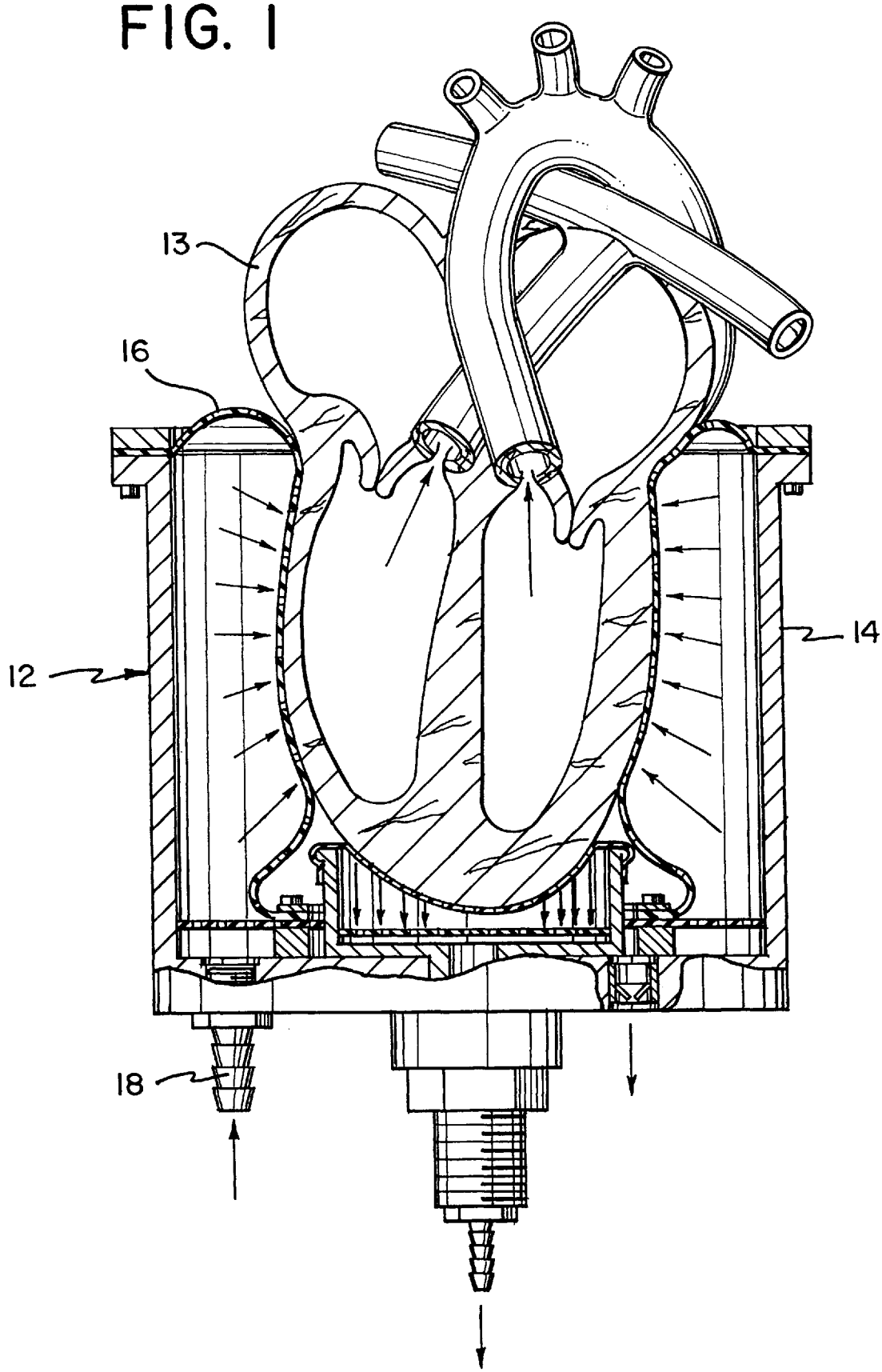
FIG. 1 is a cross-sectional view of a non-limiting example of a cardiac assistance apparatus aiding a heart to illustrate an important application for the inflation system of the present invention.

By way of example, FIG. 1 illustrates a cardiac compression apparatus 12 for assisting a heart 13 to pump blood through a vasculature by substantially uniformly compressing the heart ventricle during the systolic phase. An example of such an apparatus is disclosed in pending U.S. patent application Ser. No. 60/028,722, filed on Oct. 18, 1996, the disclosure of which is hereby incorporated by reference. The heart is placed into the apparatus which is lined with an internal inflation chamber or liner 16 that includes a port 18 for connecting to an inflation system according to the present invention.

Figure 2A:
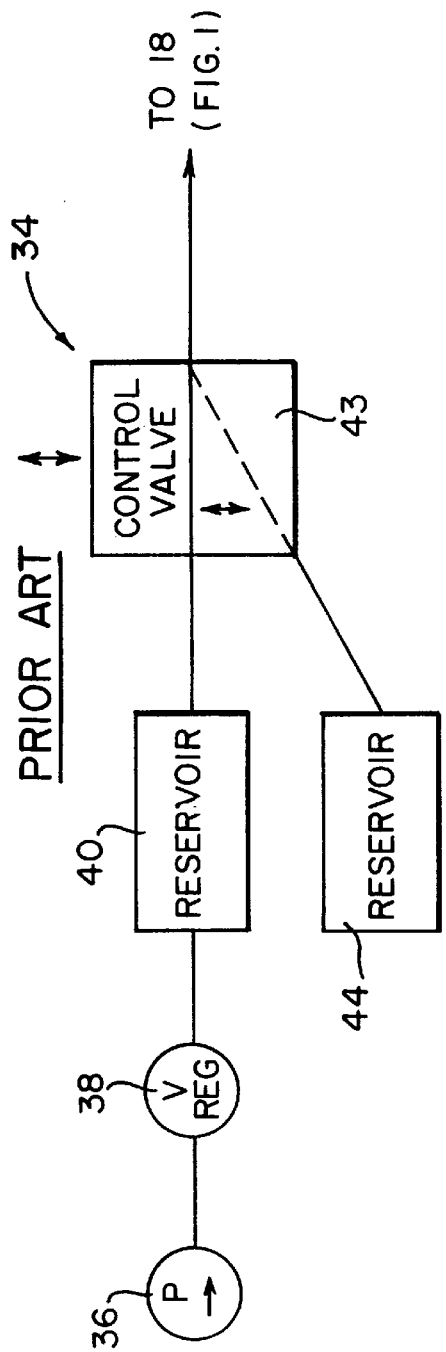
FIGS. 2A and 2B are block diagrams of a conventional inflation system.

Referring now to FIGS. 2A and 3A, a first conventional inflation system for generating a pressure profile in synchronous relation with the pumping heart 13, and generally designated 34, includes a pneumatic compressor 36 having an output coupled to a regulator 38, and a reservoir or tank 40 disposed downstream of the regulator. A first control valve 43 connects to the reservoir outlet. Control valve 43 is a two-way valve and has its output directed to the inflation chamber disposed in the cardiac compression apparatus 12 of the type shown in FIG. 1. A controller (not shown) controls the actuation of control valve 43 according to relatively precise timing such as that illustrated in FIG. 3A. During operation of the first conventional inflation system, the compressor supplies flow through the regulator, which maintains a desired pressure in the tank. Inflation of the liner 16 occurs by opening the first control valve 43 to produce an asymptotically increasing pressure transient within the chamber. The source pressure maintained within tank 40 is the desired plateau pressure. Once a predetermined duration has expired, control valve 43 is switched so that inflatable chamber port 19 of apparatus 12 is now in fluid communication with reservoir 44. Chamber 44 is simply a vent to atmosphere.

Figure 2B:
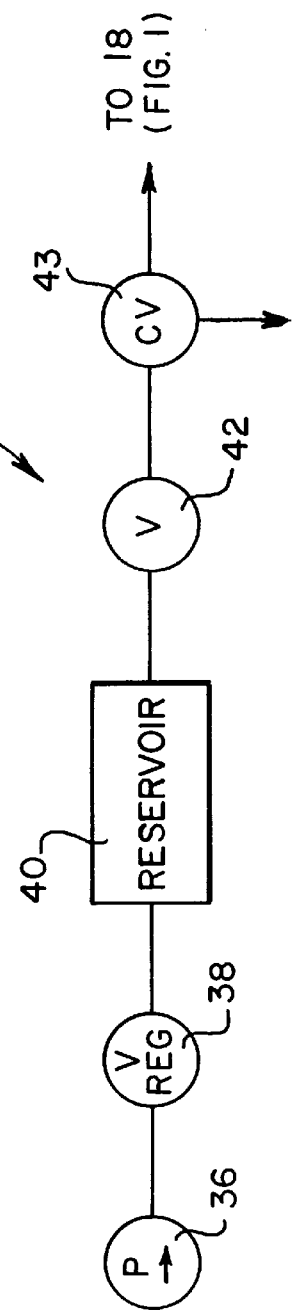

Referring now to FIGS. 2B and 3B, a second conventional inflation system for generating a pressure profile in synchronous relation with the pumping heart 13, and generally designated 34, includes a pneumatic compressor 36 having an output coupled to a regulator 38, and a reservoir or tank 40 disposed downstream of the regulator. A first control valve 42 connects to the reservoir outlet. A three-way two position distribution valve 43 is placed in downstream fluid communication with the first control valve and has its output directed to the inflation chamber disposed in the cardiac compression apparatus 12 of the type shown in FIG. 1. A controller (not shown) controls actuation of the control valves 42 and 43 according to relatively precise timing such as that illustrated in FIG. 3B.

During operation of the second conventional inflation system, the compressor supplies flow through the regulator, which maintains a desired pressure in the tank. Inflation of the liner 16 occurs by simultaneously opening both the first control valve 42 and the distribution valve 43 to produce an asymptotically increasing pressure transient within the chamber. Once a predetermined duration has expired, calculated to take into account the time required for any equilibrium effects, the control valve 42 is closed while the pressure circuit traps the pressurized gas in the liner. Following a predetermined period corresponding to the duration of the systolic cycle, the distribution valve is actuated to vent the liner to atmosphere.

Figure 4:
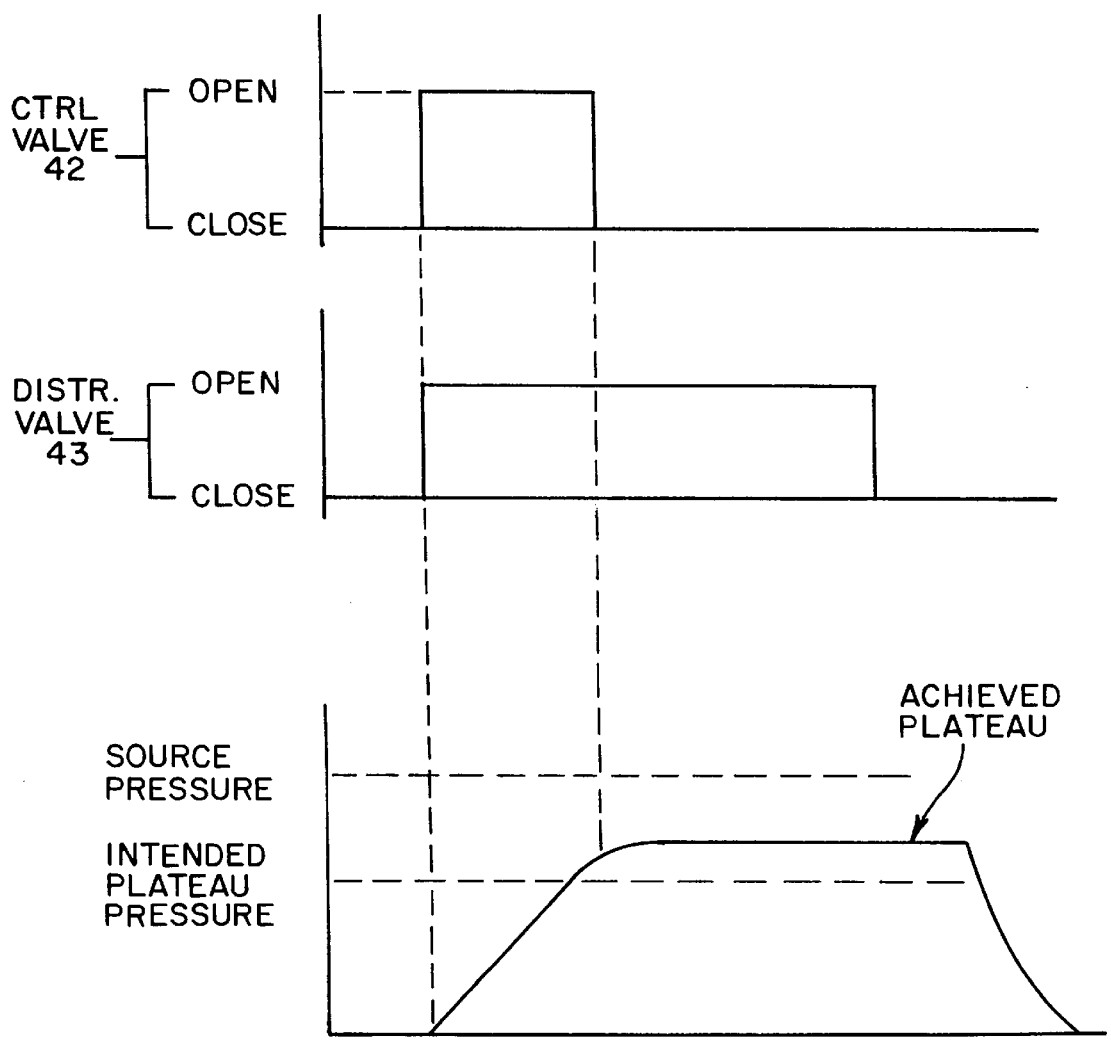
FIG. 4 is a graphical representation of an undesirable response for the conventional inflation system of FIG. 2B.

FIG. 4 illustrates the effect of a slight inaccuracy of the aforedescribed timing resulting in an undesirable overshoot of the desired plateau level. Such effects are often undesirable in cardiac compression applications due to higher pressure applied to the heart than are desired and, additionally, unexpected stresses placed upon the inflatable liner 16.

Figure 5:
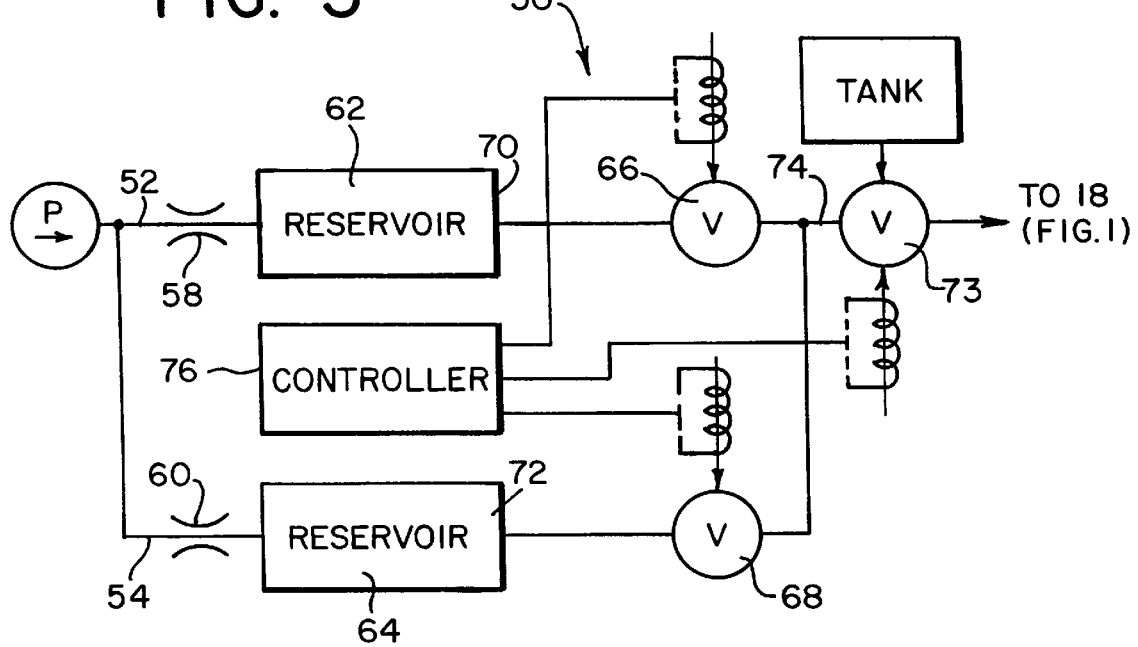
FIG. 5 is a block diagram of an inflation system according to a first embodiment of the present invention.

Referring now to FIG. 5, the inflation system according to a first embodiment of the present invention and generally designated 50, provides the capability of independently controlling the rise time and plateau level of an applied pressure pulse. The system includes a pair of pressure paths 52 and 54 disposed in parallel fluid communication with a pneumatic source 56. The pneumatic source 56 typically comprises a controllable compressor or pump capable of producing pressurized gas at pressures between the range of 6 psi to 60 psi (300 to 3000 mmHg). An additional source suitable for this application includes a pressurized pneumatic cylinder with appropriate plumbing to step down the bottled pressure or pressure from gas distribution lines frequently supplied in hospitals to a controllable level.

The pressure paths 52 and 54 include respective regulators 58 and 60 disposed downstream of the pressure source 56 and connected to respective tanks or reservoirs 62 and 64. The regulators are configured to maintain respective high and low pressure levels within the tanks. The high pressure level is typically set within the range of approximately 150 to 300 mmHg while the low range often approximates 60 to 150 mmHg. Respective control valves 66 and 68 together comprise a supply mechanism and are disposed at the tank outlets 70 and 72 and plumbed into a common supply manifold 74. The manifold connects to the a venting mechanism 73. Venting mechanism 73 is preferably a 3-way valve with manifold 74 and the conduit from tank 75 being the inputs and the conduit lending to the inflatable chamber port 18 (FIG. 1) being the output. Tank 75 may be open to a atmosphere or to a negative pressure (i.e., a vacuum). For safety considerations, venting mechanism 73 preferably defaults to being in communication with the inlet conduit from tank 75.

Figure 6:
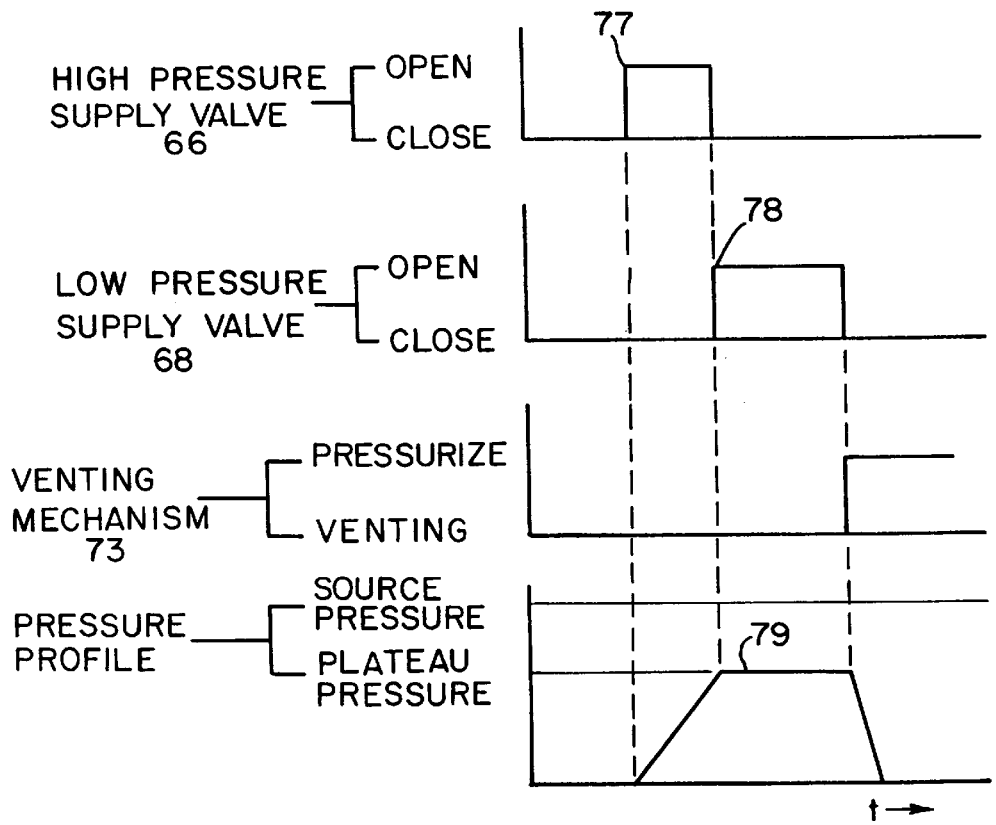
FIG. 6 is a timing diagram for the inflation system of FIG. 5 illustrated with respect to a portion of a pressure profile.

A controller 76 electrically connects to the solenoids of the respective control valves 66 and 68 to sequence the valve states according to a predetermined timing scheme illustrated in FIG. 6.

Operation of the inflation system 50 involves activating a control signal 77 (FIG. 6) to open the high pressure supply control valve 66 and opening the valve 73 to manifold 74 to pressurize the inflatable chamber 16 according to a higher magnitude transient characteristic of the predetermined high pressure. At the end of a predetermined duration, corresponding to the rise time of the pressure profile, a second control signal 78 closes the high pressure supply valve 66 while simultaneously signaling the low pressure supply valve 68 to open. The regulating action of the low pressure path quickly zeroes in the chamber pressure to that of the desired plateau pressure 79.

At the end of the systolic phase, the controller 76 returns the chamber to its pre-pressurized condition by deactivating and closing the low pressure supply control valve 68 and quickly relieving the system with venting mechanism 73 to atmospheric pressure to approximate the release phase of the heart pressure profile. The entire cycle repeats within a relatively short period approximating the range 400 to 1000 milliseconds to correspond with the cyclic activity of the heart.

Figure 7:
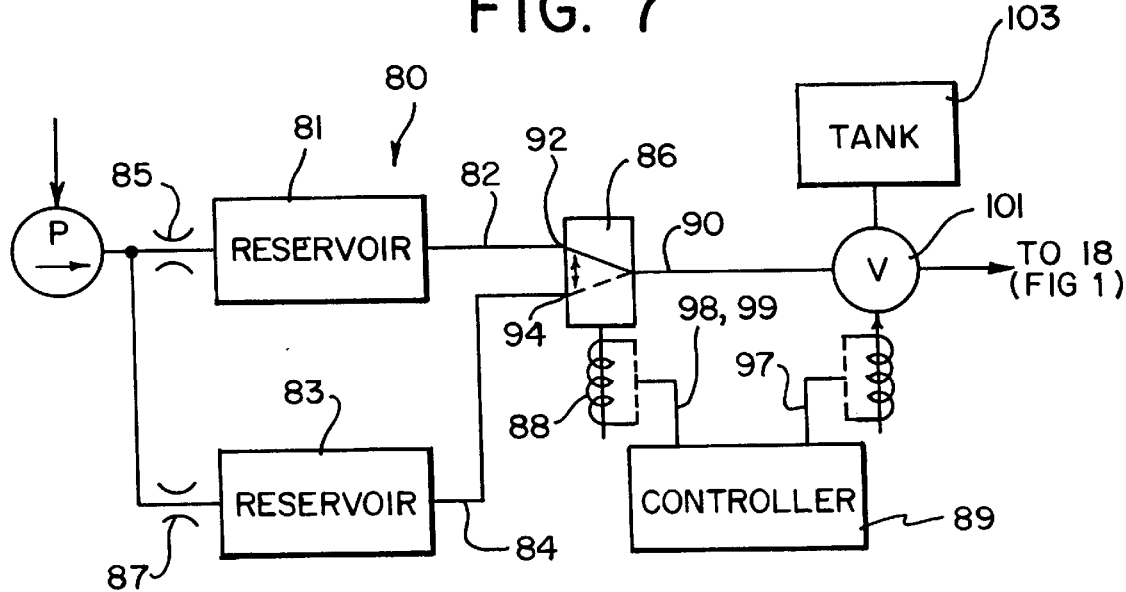
FIG. 7 is a block diagram of an inflation system according to a second embodiment of the present invention.

With reference to FIG. 7, a variation of the present invention according to a second embodiment and generally designated 80, conveniently reduces the number of components necessary to implement the invention. Like the first embodiment illustrated in FIG. 5, the variation includes respective high and low pressure paths 82 and 84 driven by a single compressor P and including respective reservoirs 81 and 83, and respective regulators 85 and 87. However, unlike the aforedescribed embodiment, the outputs of the tanks terminate in a single switching valve 86 that comprises a supply mechanism and includes a solenoid actuator 88 responsive to a controller 89 to switch the valve output 90 between respective high and low pressure inputs 92 and 94. Output 90 connects to a venting mechanism 101 for introducing pressure from output 90 or atmospheric pressure from tank 103 into the inflatable chamber 16 (FIG. 1). Tank 103 may be open to atmosphere or to a negative pressure. Switching valve 86 and venting mechanism valve 101 together comprise a supply mechanism.

Figure 8:
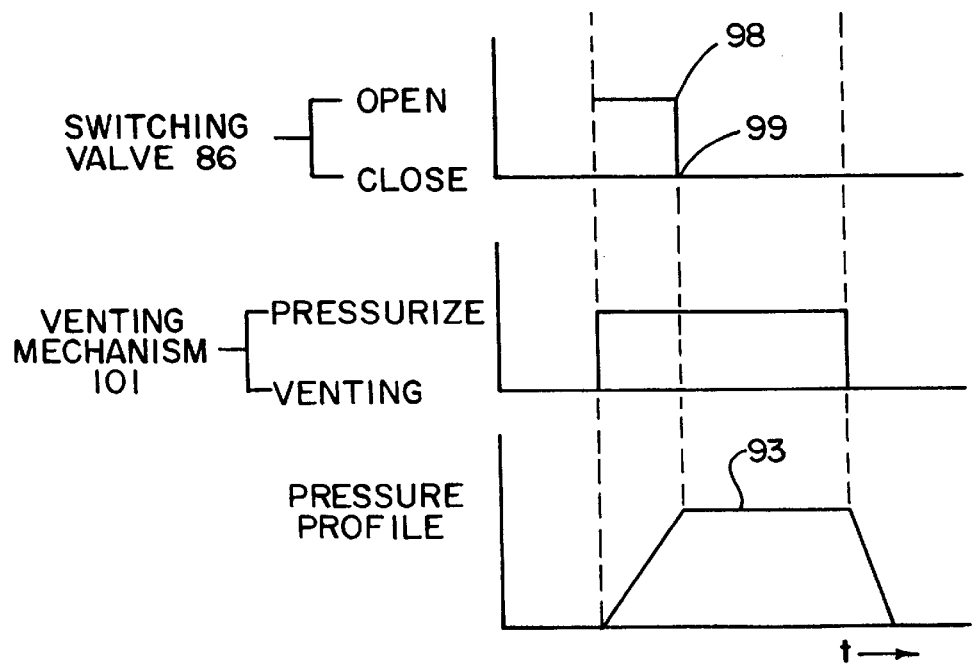
FIG. 8. is a timing diagram for the inflation system of FIG. 7 illustrated with respect to a portion of a pressure profile.

Referring now to FIG. 8, in the timing scheme utilized to actuate the system 80, the switching valve 86 is expected to be initially set with the low pressure path 84 open through the output 90. Initiation of the pressure profile then begins by actuating the venting mechanism 101 with signal 97 and the switching valve 86 with signal 98, to expose the chamber to the set high pressure. Following a pre-set duration corresponding to the profile rise time, the output of the switching valve 86 switches, with signal 99, back to the normally open position thereby introducing pressurized gas from the low pressure path 84 into the chamber to settle on the pre-set low pressure level corresponding to the plateau level 93. Following the pre-set desired duration for the plateau level, a venting mechanism 101 is actuated by the controller to quickly relieve the system corresponding to the release phase of the heart profile.

Referring now to FIG. 9, the number of components necessary to carry out the general principles of the present invention may be further minimized in accordance with a third embodiment of the present invention, generally designated 100. The system includes a pneumatic source 102 for pressurizing a reservoir 104 having a supply mechanism 106 and a relief mechanism 120.

Pneumatic source 102 implemented in the third embodiment of the present invention typically comprises a controllable compressor or pump capable of producing pressurized gas at pressures between the range of 60 to 300 mmHg. An additional source suitable for this application includes a pressurized pneumatic cylinder with appropriate plumbing to step down the bottled pressure to a controllable level. Alternatively, pressurized gas that is frequently supplied by hospitals, in the form of gas distribution lines, may be used as the pressure source.

The pneumatic source 102 connects to the tank or reservoir 104 disposed in fluid communication with the supply mechanism 106 and the relief or bypass mechanism 120. The supply mechanism 106 typically comprises a three-way control valve responsive to activation of a solenoid actuator 108, which actuation is controlled by control unit 122. The output of three-way control valve 106 is connected to a pressure output 110, which is connected to the inflatable chamber port 18 (FIG. 1). The input to control valve 106 is either connected to tank 104 or to tank 105. Tank 105 may be open to atmosphere or connected to a negative (i.e., a vacuum) pressure to assist in deflating the liner during the diastolic phase. Bypass mechanism 120 typically comprises a back pressure regulator 114 connected to a bypass port on the reservoir and a control valve 116 responsive to a solenoid 118 and positioned at the regulator outlet 120.

The respective control valve solenoids 108 and 118 electrically connect and are responsive to a controller 122 that sends respective control signals 124 and 126 to the control valves according to a predefined timing scheme, shown in FIG. 10. The timing scheme, in concert with the pressure levels, conveniently enables independent control of the rise time and the plateau level with a single tank and regulator.

Further referring to FIGS. 9 and 10, during operation of the inflation system 100, the controller 122 initiates the start control signal 126 to open valve 116 (i.e., in fluid communication with tank 104) and close valve 106 (i.e., in fluid communication with tank 105). Valve 116 is preferably set so that when it is open, the pressure within tank 104 is at the plateau pressure ("$P_{plateau}$"). By merely changing regulator's 114 setpoint, the plateau level can be easily controllable to a relatively high degree of precision. When valves 116 and 106 are closed, tank 104 is essentially at the supply pressure of source 102 ("$P_{supply}$") While still maintaining valve 106 closed, valve 116 is closed causing the pressure within tank 104 to reach $P_{supply}$, which is greater than $P_{plateau}$. Controller 122 opens the supply valve 106 and exposes the line 110 connected to the interior of chamber 18 (FIG. 1) to pressurized gas in the range of 150 to 500 mmHg, which is equal to $P_{supply}$. Simultaneously, or after a short delay of between approximately 10 milliseconds to 100 milliseconds, valve 116 is opened by control signal 126 to cause the pressure within chamber 18 to approach $P_{plateau}$, without any overshoot. The pressure within chamber 18 increases exponentially toward $P_{supply}$, until the second control signal 126 is sent by the controller to open the control valve solenoid 118. The timed duration between the control signals corresponds to the rise time of the pressure profile. Those skilled in the art will recognize the convenient adjustability of the compressor pressure and the timed duration to vary the rise time as necessary to closely approximate the corresponding natural rise time of the systolic cycle of the heart.

At the end of the systolic phase, the controller 122 returns the chamber to its pre-pressurized condition by deactivating and closing the supply control valve 106 and quickly venting the system to atmospheric pressure, thereby releasing the pressure in the chamber. The entire cycle repeats within a relatively short period, typically within approximately 400 to 1000 milliseconds, corresponding to the cyclic activity of the heart.

Figure 11:
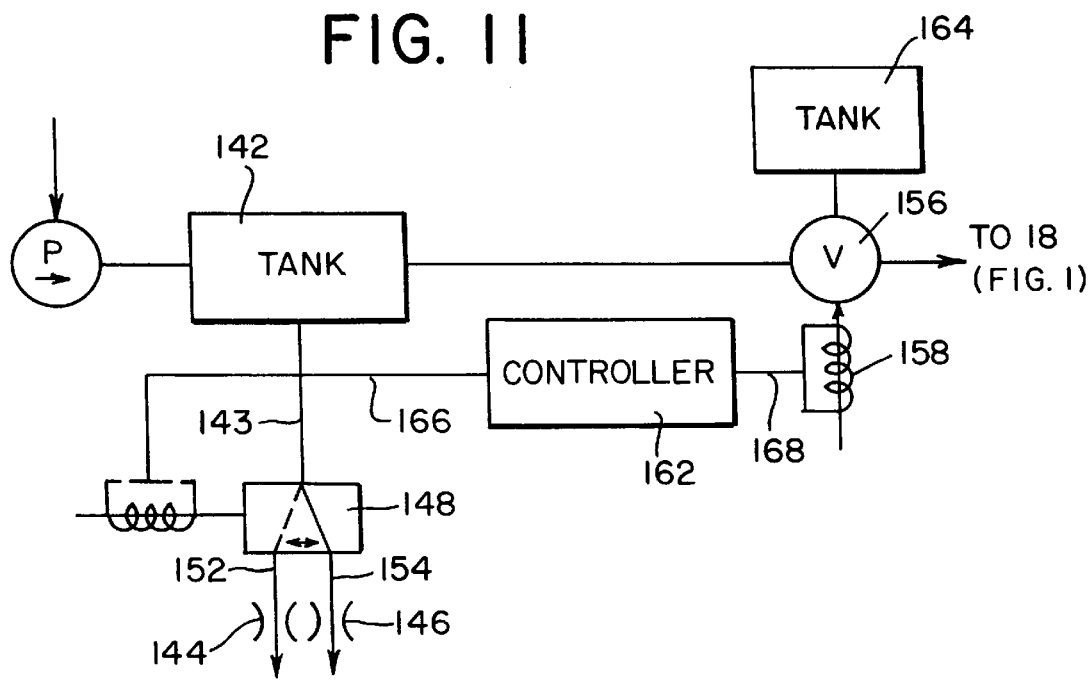
FIG. 11 is a block diagram of an inflation system according to a fourth embodiment of the present invention; and, FIG. 12 is a timing diagram for the inflation system of FIG. 11 illustrated with respect to a portion of a pressure profile.

With reference to FIG. 11, another variation of the present invention according to a fourth embodiment, and generally designated as 160, is illustrated. In this embodiment, only one reservoir 142 is required. The output of pressure source 140 is in direct fluid communication with reservoir 142. A first bypass output path places tank 142 in fluid communication with either a first high pressure path 152 or a second low pressure path 154 through three-way switching valve 148. Regulators 144, 146 are connected to paths 152, 154, respectively. Regulator 144 sets the pressure within line 152 at a predetermined pressure above the plateau pressure. Regulator 146 sets the pressure within line 154 at the plateau pressure. A single switching valve 148 is connected to the inputs of fluid lines 152, 154, respectively. A controller 162 switches valve 148 so that tank 142 is either in fluid communication with high pressure line 152 or plateau pressure line 154.

A second output line 150 fluidly connects the output of tank 142 to a supply mechanism or valve 156. Supply valve 156 is similar to supply valve 106 illustrated in FIG. 9. Thus, valve 156 is a three-way valve. The input to control valve 156 is either connected to tank 142 or tank 164. Tank 164 may be open to a atmosphere or to a negative pressure.

Figure 12:
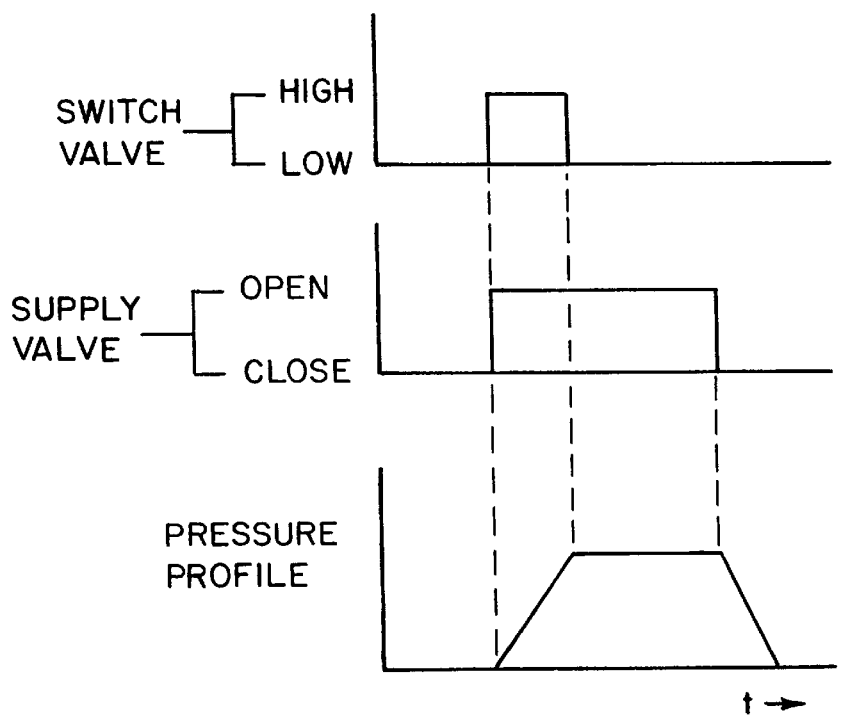

Referring now to FIGS. 11 and 12, during operation of the inflation system 160, controller 162 initiates a start control signal 166 to switch valve 148 so that it is in fluid communication with high pressure line 152. Thereafter, control signal 122 initiates start control signal 168 to open supply valve 156 so that the liner is in fluid communication with tank 142 via output line 150. Simultaneously, or after a short delay of between approximately 10 milliseconds to 100 milliseconds, controller 162 initiates a signal to switch valve 148 so that tank 142 is now in fluid communication with plateau line 154. Thus, the pressure within tank 142 will be immediately adjusted to the plateau pressure so that the pressure within chamber 18 approaches $P_{plateau}$, without any over shoot. As illustrated in FIG. 12, the pressure within chamber 18 exponentially rises towards the pressure set within high pressure line 152, until a signal is sent by the controller to switch valve 148 so that the tank is now in fluid communication with the plateau pressure line 154. Those skilled in the art will recognize that while the rise to the high pressure as illustrated by ramped portion 170 in the pressure profile of FIG. 12, is essentially exponential, this line is practically a straight line because of the relatively high setting of the high pressure within line 152. At the end of this diastolic phase, the controller 162 returns the chamber to its prepressurized position by switching supply valve 156 and quickly venting chamber 18 to either atmospheric pressure or to a negative pressure, as desired.

While the aforedescribed embodiments of the present invention are illustrated with respect to an independently controllable rise time for a pressure profile, it will be understood that the invention is applicable to controlling rise times for a variety of diagnostic waveforms indicating cardiac parameters with respect to time, including for example compression or force profiles.

Those skilled in the art will appreciate the many advantages afforded by the inflation system of the present invention. Of particular significance is the capability of independently controlling the rise time and plateau level of the pressure profile. With this feature, the pressure pulse can be customized to substantially match a patient's pressure profile to place the system in a more synchronous rhythm with the natural cyclic pumping of the heart. As a result, instances of destructive interference between the assistance apparatus and the heart itself are minimized, thereby maximizing the effective assistance provided to the heart.

The present invention also provides the benefit of incorporating a straightforward design to carry out the functionality with a minimum number of mechanical components. By minimizing the number of components, costs involved in the purchase and operation of the system are dramatically reduced. Moreover, minimizing the number of mechanical components also serves to reduce the overall size and complexity of the inflation system, making the system highly desirable for portable applications. Because of the relatively few high maintenance components and corresponding plumbing lines, system reliability is substantially improved.

While the invention has been particularly shown and described with reference to the preferred embodiments thereof, it will be understood by those skilled in the art that various changes in form and detail may be made therein without departing from the spirit and scope of the invention.

What is claimed is:

1. An inflation system for independently controlling the rise time and plateau level of a pressure cycle profile applied to an inflatable chamber, said system including:
    a pneumatic source for pressurizing fluid at a predetermined pressure;
    a pressure path disposed in fluid communication with said source and including a regulation device for establishing respective high and low pressure levels; and
    a supply mechanism disposed at the output of said pressure path and operative to alternately expose said chamber to said high and low pressure levels according to predetermined switchable durations to define said rise time and plateau levels.

2. An inflation system according to claim 1 wherein:
said pneumatic source comprises an air compressor.

3. An inflation system according to claim 1 wherein:
said pneumatic source comprises a pre-pressurized pneumatic cylinder.

4. An inflation system according to claim 1 wherein:
said pneumatic source comprises a pump.

5. An inflation system according to claim 1 wherein:
said pneumatic source comprises a pneumatic distribution line.

6. An inflation system according to claim 1 wherein:
said predetermined high pressure level is within the range 150 to 300 mmHg; and
said low pressure level is within the range 60 to 150 mmHg.

7. An inflation system according to claim 1 wherein:
said pressure path comprises
    a reservoir having an inlet disposed in fluid communication with said pneumatic source and
    a controllable bypass mechanism disposed in fluid communication with said reservoir and operative, when said duration expires, to controllably relieve the pressure in said reservoir to a second pressure defining said plateau level.

8. An inflation system according to claim 7 wherein:
said reservoir comprises a tank; and
said supply mechanism comprises a supply control valve disposed downstream of said tank.

9. An inflation system according to claim 7 wherein:
said bypass mechanism comprises a regulator having an inlet connected to said reservoir, and a bypass control valve connected to the outlet of said regulator.

10. An inflation system according to claim 9 and further including:
    a controller for generating predefined sequenced signals to control said supply mechanism and said bypass control valve.

11. An inflation system according to claim 10 wherein:
said controller produces respective first and second signals according to timing defined by said switchable durations,
said supply mechanism operates responsive to said first signal to expose said chamber to said predetermined pressure according to an essentially exponential pressure increase; and
said bypass mechanism operates responsive to said second signal to relieve said chamber pressure to said plateau level.

12. An inflation system according to claim 1 wherein:
said pressure path includes
    a high pressure path connected to said pneumatic source and including a high pressure reservoir and a regulator to maintain a first pressure in said reservoir; and
    a low pressure path connected to said pneumatic source and disposed in parallel relationship with said high pressure path and having a low pressure reservoir and a low pressure regulator to maintain a second pressure in said reservoir.

13. An inflation system according to claim 12 further comprising:
    a switching valve including a first inlet and a second inlet connected to said high and low pressure paths, respectively, and an outlet connected to said chamber and operative to switch between said first and second pressure paths to selectively control the pressure within said chamber to correspondingly control said rise time and plateau level.

14. An inflation system according to claim 13 and further including:
    a controller for generating predefined sequenced signals to control said switching valve.

15. An inflation system according to claim 14 wherein:
said controller produces respective first and second signals according to timing defined by said switchable durations; and
said switching valve operates responsive to said first signal to open said high pressure path and expose said chamber to said first pressure according to an essentially exponential pressure increase and responsive to said second signal to close said high pressure path and simultaneously open said low pressure path to expose said chamber pressure to said second pressure.

16. An inflation system according to claim 13, further comprising:

a tank being in fluid communication with one of an atmospheric pressure and a negative pressure, said tank having an outlet;

a venting mechanism including a first inlet and a second inlet end connected to said outlet of said switching valve and to said outlet of said tank, respectively, said venting mechanism including an outlet connected to said chamber.

17. An inflation system according to claim 16, wherein said venting mechanism defaults to being in fluid communication with said outlet of said tank.

18. An inflation system according to claim 12 wherein:

said high pressure level is within the range 150 to 300 mmHg; and said low pressure level is within the range 60 to 150 mmHg.

19. An inflation system according to claim 12, further comprising:

a first control valve connected to said high pressure path and a second control valve connected to said low pressure path; and an outlet of said first control valve and an outlet of said second control valve each being in communication with a common supply manifold.

20. An inflation system according to claim 19, further comprising:

a tank being in fluid communication with one of an atmospheric pressure and a negative pressure, said tank having an outlet;

a venting mechanism including a first inlet and a second inlet connected to said manifold and to said outlet of said tank, respectively, said venting mechanism including an outlet connected to said chamber.

21. An inflation system according to claim 20, wherein said venting mechanism defaults to be in fluid communication with said outlet of said tank.

22. An inflation system for independently controlling the rise time and plateau level of a pressure cycle profile applied to an inflatable chamber, said system including:

a pneumatic source for pressurizing fluid at a predetermined pressure;

a pressure path disposed in fluid communication with said source and including a regulation device for establishing respective high and low pressure levels;

a reservoir having an inlet disposed in fluid communication with said pneumatic source;

a controllable switching valve disposed in fluid communication with said reservoir and operative when said duration expires, to controllably relieve the pressure in said reservoir to a second pressure defining said plateau level; and a supply mechanism disposed at the output of said pressure path and operative to alternately expose said chamber to said high and low pressure levels according to predetermined switchable durations to define said rise time and plateau levels.

23. An inflation system according to claim 22 wherein:

said reservoir comprises a tank; and said supply mechanism comprises a supply control valve disposed downstream of said tank.

24. An inflation system according to claim 22, wherein said switching valve comprises a three-way valve having a first inlet being a first pressure path that is regulated to said high pressure level and a second inlet that is connected to a second pressure path that is regulated to said low pressure level and an outlet that is connected to said reservoir.

25. An inflation system according to claim 24, further including a controller for generating predefined sequence signals to control said supply mechanism and said switching valve.

26. An inflation system according to claim 25, said controller produces respective first and second signals according to timing defined by said switchable durations, said supply mechanism operates responsive to said first signal to expose said chamber to said predetermined pressure according to an essentially exponential pressure increase; and said switching valve operates responsive to said second signal to relieve said chamber pressure to said plateau level.

27. A heart assistance system for supporting and assisting the cyclic pumping of a heart, said compression system including:

a cardiac compression apparatus having a support cup and an internal inflation chamber for uniformly compressing said heart; and an inflation system for applying a pressure pulse to said inflation chamber and place said heart in cyclic compression by independently controlling the rise time and the plateau level of a pressure pulse, said inflation system including a pneumatic source for pressurizing fluid at a predetermined pressure;

a pressure path disposed in fluid communication with said source and including a regulation device for establishing respective high and low pressure levels; and a supply mechanism disposed at the output of said pressure path and operative to alternately expose said chamber to said high and low pressure levels according to predetermined switchable durations to define said rise time and plateau levels.

28. A method of independently controlling the rise time and the plateau level of a pressure cycle applied to an inflatable liner disposed in a cardiac compression apparatus, said method including the steps of:

exposing said liner to a first pressure from a pressure reservoir to essentially exponential increase the pressure within said liner for a controllable duration defining said rise time;

switching the pressure in said reservoir following expiration of said duration to a constant second pressure defining said plateau level.

29. A method according to claim 28 wherein:

said switching step includes relieving the pressure in said reservoir with a bypass mechanism comprising a regulator disposed in fluid communication with said reservoir, and a control valve connected to the output of said regulator.

30. A method of assisting the pumping of a heart, said pumping corresponding to a definable systolic cycle, said method including the steps of:

selecting a cardiac compression apparatus having a support cup and an inflatable liner;

exposing said liner to a first pressure from a pressure reservoir to exponentially increase the pressure within said liner for a controllable duration defining said rise time;

switching the pressure in said reservoir following expiration of said duration to a constant second pressure defining said plateau level.

31. A method according to claim 30 wherein:

said selecting step includes providing an inflation system having a pneumatic source for pressurizing fluid at a predetermined pressure; a pressure path disposed in fluid communication with said source and including a regulation device for establishing respective high and low pressure levels; and a supply mechanism disposed at the output of said pressure path and operative to alternately expose said chamber to said high and low pressure levels according to predetermined switchable durations to define said rise time and plateau levels.

* * * * *